United States Patent [19]
Palumbo

[11] Patent Number: 5,947,913
[45] Date of Patent: Sep. 7, 1999

[54] METHOD FOR TREATING THE HUMAN KNEE

[76] Inventor: Pasquale M. Palumbo, 8206 Leesburg Pike, Vienna, Va. 22182

[21] Appl. No.: 08/964,826

[22] Filed: Nov. 5, 1997

Related U.S. Application Data

[63] Continuation-in-part of application No. 08/818,555, Mar. 14, 1997, Pat. No. 5,807,298, which is a continuation-in-part of application No. 08/378,606, Jan. 26, 1995, Pat. No. 5,613,943.

[51] Int. Cl.⁶ .................................. A61F 5/00; A61N 1/18
[52] U.S. Cl. .................................. 602/2; 602/26; 607/48
[58] Field of Search .................... 602/24, 23, 26, 602/60, 61, 62; 2/24, 62; 128/892; 607/46, 48, 49, 72, 74, 115, 149, 152

[56] References Cited

U.S. PATENT DOCUMENTS 5,487,759  1/1996  Bastyr et al. ............................ 607/149
5,613,943  3/1997  Palumbo ................................... 602/62

OTHER PUBLICATIONS

Smith and Newphew, Donjoy Products Catalog, pp. 25–29, 1994.

*Primary Examiner*—Richard J. Apley
*Assistant Examiner*—Kim M Lee
*Attorney, Agent, or Firm*—Jim Zegeer

[57] ABSTRACT

A method and system for treating the human knee having a patella and musculature including vastus medialis obliquus (VMO), rectus femoris (RF), and vastus lateralis obliquus (VLO) muscles. A patella tracking medial force is applied to the patella, the medial force tracking vertical and horizontal movements of the patella. A current of selected wave shape, amplitude, duration and frequency is applied to the vastus medialis obliquus (VMO) muscle so as to stimulate the VMO muscle and thereby tend to correct the reuslting vector force of the VMO, VLO, and RF muscles on the patella. Preferably the current is applied transcutaneously.

2 Claims, 1 Drawing Sheet

METHOD FOR TREATING THE HUMAN KNEE

REFERENCE TO RELATED APPLICATION

This application is a continuation-in-part of my application Ser. No. 08/818,555 filed Mar. 14, 1997, now U.S. Pat. No. 5,807,298, for DYNAMIC PATELLA BRACE AND METHOD which is a continuation-in-part application of my application Ser. No. 08/378,606 filed Jan. 26, 1995 entitled DYNAMIC PATELLA BRACE WITH FLOATING PATELLA PAD, now U.S. Pat. No. 5,613,943 (both incorporated herein by reference).

There are numerous conditions for which bracing is required, both braces for the extensor mechanism, i.e., the patella, as well as braces for the collateral and cruciate ligament stabilities. These braces have been successful over the years in clinical use. The present invention adds another modality to rehabilitating the knee.

There are numerous varieties of knee braces for treating various limbs with joint conditions. In my U.S. Pat. No. 4,296,744 (incorporated herein by reference) I disclose a dynamic patella brace which is very useful for both diagnosis and treatment of patella conditions. In a typical device, a sleeve member, made of elastic fabric such as nylon coated neoprene or Lycra® provides compressive force and warmth. In my U.S. Pat. No. 4,296,744, force is applied to the patella in a medial direction for diagnosis and/or treatment of the knee. In my U.S. Pat. No. 5,613,994 and my application Ser. No. 08/818,555, the patella force is floatingly applied and more closely tracks vertical and horizontal movement of the patella.

Use of electrical currents for pain relief and muscle rehabilitation in combination with a brace or support device is known in the medical arts (see Bastyr et al, U.S. Pat. No. 5,487,759).

Thus, the object of the invention is to provide an improved method and apparatus for treatment of the knee.

The present invention provides a knee brace which applies a medial force on the patella, the medial force tracking patella movements vertically and horizontally and, at the same time, applies a muscle stimulation (MS) and/or rehabilitating electrical current to the vastus medialis obliquus (VMO) so that the vastus medialis obliquus (VMO) muscle is strengthened and thereby tends to correct the vector forces of the vastus medialis obliquus, the vastus lateral obliquus, and the rectus femoris muscles.

The term "patella force device" is intended to encompass any device which applies or transfers external medial force to the patella or knee cap, as disclosed, for example, in any of my above-identified patent and application. Other devices for applying or transferring a medial force to the patella are intended to be included herein. The basic objective is to allow or cause the applied medial force to track vertical and horizontal movements of the patella as closely as possible substantially through the full range of knee movement.

Many knees have patellofemoral instability for numerous reasons, i.e., developmental, hereditary, traumatic, etc., in which the patella tracks abnormally, generally in a lateral direction. One of the main causes of lateral displacement of the patella is a weak or dysplastic vastus medialis obliquus muscle. Another reason for bracing is that anterior cruciate as well as medial collateral bracing prevents the abnormal shifting of bones. Most of these conditions are associated with weakened musculature, and the clinical treatment generally requires use of the brace and patient's compliance in rehabilitating muscle groups to assist in the correction of the instabilities, i.e. strengthening of the hamstrings with anterior cruciate instability, strengthening of the quadriceps with posterior cruciate instability.

Generally, injuries to the knee, as well as injuries to the lower extremity as well as postoperative procedures to the lower extremity or knee, result in quadriceps atrophy. Immobilization of the lower extremity results in early and progressive atrophy of various muscle groups, particularly the quadriceps.

The present invention facilitates and accelerates the rehabilitative time and degree of the rehabilitation of the lower extremity by use of the bracing means which are essentially mechanical with the combined use of the neurophysiological adjunct of neuromuscular electrical stimulation. In the case of the patella stabilizing brace, the electrical generator can be mounted in a box placed in a sleeve or pocket attached to the brace with the electrodes passing through the sleeve to the vastus medialis obliquus (VMO) or other associated muscle group(s), if necessary. The patient, while wearing the brace and being active, would also, at intermittent periods, stimulate voluntarily the VMO muscle groups through the use of the generator through the electrode in a transcutaneous manner. In addition, electrodes could be applied to other muscle groups as the selective atrophy would dictate.

In cases where anterior cruciate stability is involved, the electrodes could also be placed amongst other locations over the hamstring tendons to strengthen this muscle group, which is important in ACL rehabilitation. The electrodes would be placed, or just mentioned, on the hamstrings and can be alternating with stimulation of the quadriceps.

The electrode stimulation is transcutaneous and preferably of a faradic-type current, though galvanic-type stimulation could be used but has its negative characteristics. Subcutaneous application of the current is within the broader scope of the invention.

While the patellar stabilizing brace provides a dynamic mechanical assistance to the extensor mechanism in holding the patella in the trochlea during the full range of physiologic motion, it has been felt and shown to cause increased proprioceptive awareness and enhance vastus medialis obliquus (VMO) firing by creating a more comfortable environment for the patella while held in the reduced position by the brace. The patient is advised to rehabilitate by selected limited extension exercises with resistance on the ankle. Many patients are not compliant; others have patellofemoral chondromalacia which causes pain during rehabilitation and are hesitant to do so. Muscle stimulation, combined with the wearing of the stabilizing brace would provide increased rehabilitative qualities in that the wearer would be stimulating his VMO or other selected muscle voluntarily with the use of the transcutaneous stimulator as an adjunct to his voluntary muscular contraction. This would accelerate and enhance the rehabilitation process. Muscle stimulators with the same principle would be placed in various types of knee bracing, preferably including patella bracing, ACL and MCL bracing. Knee immobilizers are notorious for causing muscle atrophy in the injured knee, and the transcutaneous muscle stimulator would assist in either inhibiting or preventing harmful deterioration of the muscle mass while the underlying pathologic condition is healing with the assistance of the immobilization itself. Various range of motion rehabilitation braces would also contain the transcutaneous muscle stimulator to enhance voluntary muscle rehabilitation.

With respect to the electrical stimulation, recently smaller units are progressively being reduced in size to provide the electrical energy for the electrodes. These units would be as small as available and attached to the brace unit by hook-and-loop Velcro® fasteners or with a pocket with easy accessibility to the patient. The electrodes can emerge from the sleeve or bracing device and either penetrate it or pass beneath or above it. It can be used during the day while the brace is being worn and at night during rest, if necessary.

This can also be applied to TENS units which are helpful in the diminution of pain. So, along with the muscle stimulator, a TENS units can be used with the brace. A unit that provides transcutaneous muscle stimulation as well as a TENS unit to diminish pain, combined with a knee brace with a means to apply a tracking medial force to the patella according to the invention, has not been available before.

Thus, knee bracing systems which include a transcutaneous muscle stimulator unit with electrodes or a TENS unit, the former to assist in the rehabilitation of the muscle for the reasons disclosed herein, with the latter to reduce pain, either both or individually, as needed, would be piggybacked onto the system to represent an integral part of the patellar knee bracing system. This would represent an extension of the various therapeutic modalities available to the therapist or the orthopaedist which heretofore have been provided separately but never in a single unit which could provide both accepted modalities of treatment.

DESCRIPTION OF THE DRAWINGS

The above and other objects, advantages and features of the invention will become more apparent when considered with the following specification and accompanying drawings wherein.

DETAILED DESCRIPTION

Figure 1:
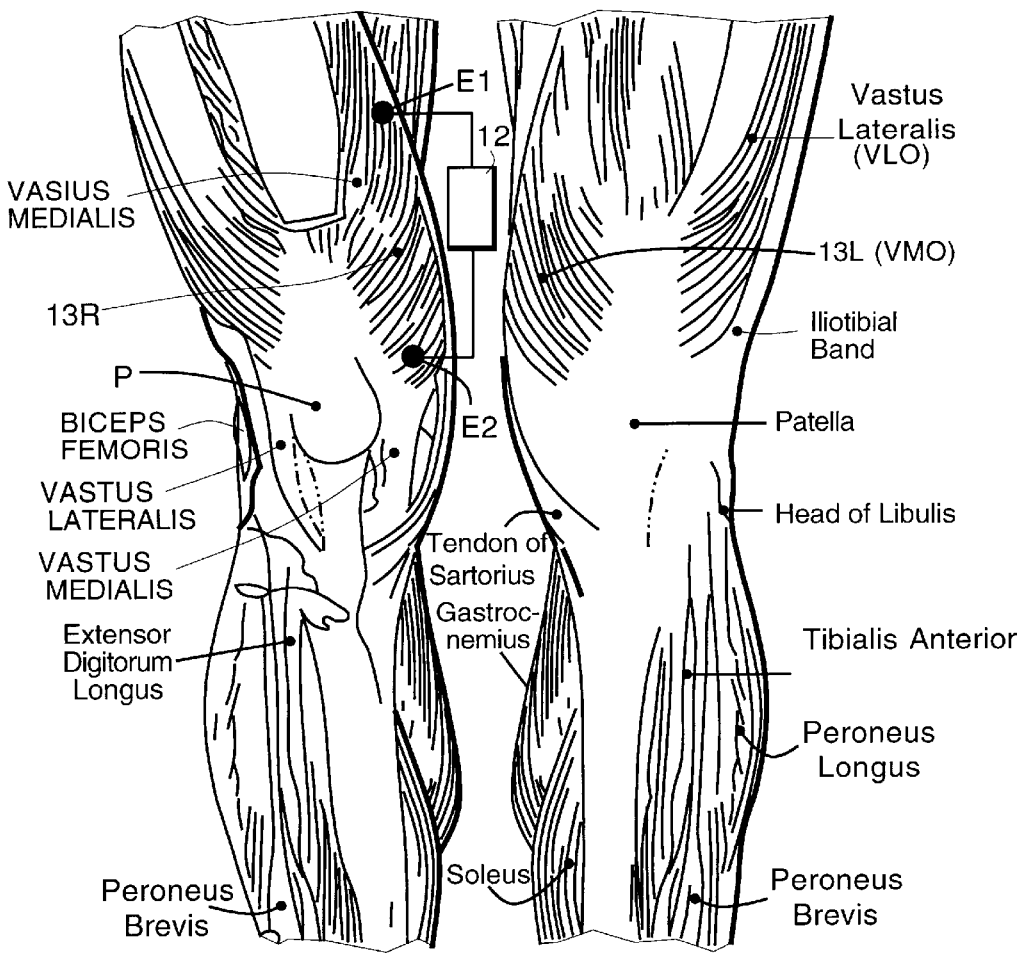
FIG. 1 is a line drawing of the left and right knee showing the various muscle groups and electrode placement for the preferred embodiment of the invention along with an indication of the medial force MF applied to the patella.
Figure 2:
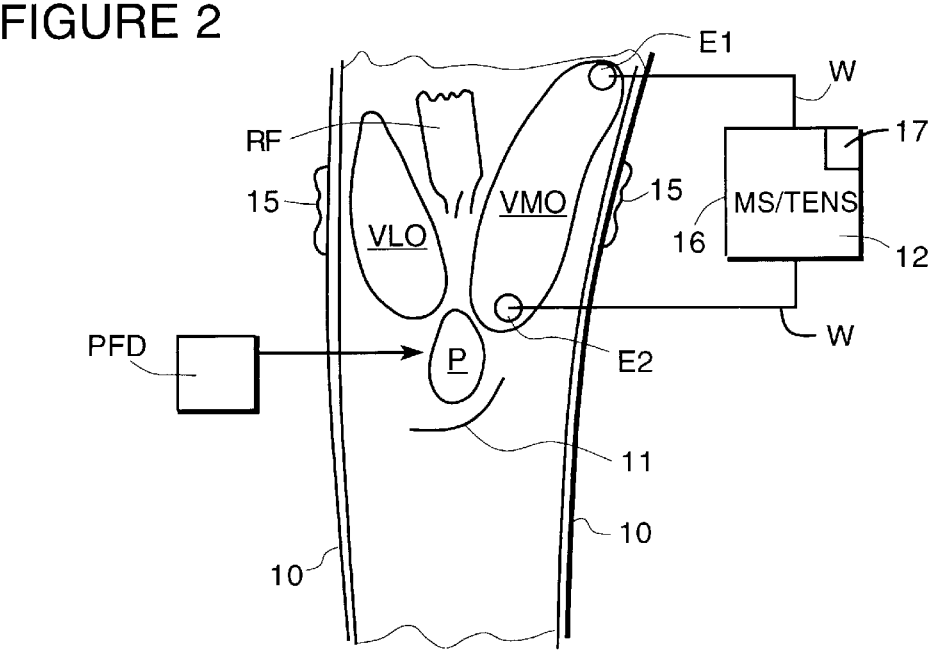
FIG. 2 is a schematic diagram of a knee showing the application of electrical currents to the VMO muscle and the patella tracking force.

Referring to the drawings, a conventional compressive-type knee sleeve 10 preferably a nylon fabric coated neoprene having four-way stretch or Lycra®, elastic, etc. has an aperture (indicated at 11) so that compressive forces on the patella are minimized and resulting in compressive support and warmth in treatment of various relatively minor knee problems. In this embodiment, patella buttresses or pads are optional. A source 12 of electrical current having a predetermined medically effective amplitude, wave shape and frequency, whether faradic or galvanic is applied to the vastus medialis obliquus (VMO) muscle 13 by upper electrode E1, and lower electrode E2 so as to stimulate the VMO muscle. As illustrated, the source 12 of electrical current is in a housing H having Velcro® loop 15 and hook 16 fastening. An operating switch 17 is used to turn the source "on" and "off". Wiring W connects the electrical current to the electrodes E1 and E2 and may be embedded in the sleeve material. It will be appreciated that while hook and loop fasteners are employed in this embodiment, the electrical components can be incorporated in a pouch or pocket (not shown) or otherwise mounted on the sleeve 10, while compression and warmth are being applied to the knee, and a medially directed patella force is being applied to the knee and in such manner as to track both vertical and horizontal movement of the patella. Electrodes E1 and E2 apply a galvanic current to the vastus medialis obliquus (VMO) muscle. In the preferred embodiment, the electrodes E1 and E2 are applied to the top (origin) of the vastus medialis obliquus muscle, and the electrode E2 is applied at the insertion or lower end of the vastus medialis obliquus muscle. The effect is that unbalanced vector forces caused by the vastus lateralis obliquus and the rectus femoris muscles are corrected by the electrically stimulated vastus medialis obliquus muscles while a tracking medial force is being applied to the patella by means of the patella force device preferably of the type disclosed in my U.S. Pat. No. 5,613,943 for DYNAMIC PATELLA BRACE WITH FLOATING PATELLA PAD. In the present application, the patella of the human knee is dynamically stabilized for diagnosis and treatment by applying compressive pressure on the knee and applying a medial pressure along a path automatically tracking vertical and horizontal movement of the patella through the functional physiological range of flexion and movement of the knee. By adding the application of a current to the vastus medialis obliquus (VMO) muscle, while the medial patella force is applied, a much more effective treatment of the knee is provided as when considered as compared to either treatment alone.

While I have shown and described a preferred embodiment of the invention, it will be appreciated that other embodiments, adaptations and modifications of the invention will be apparent to those skilled in the art.

What is claimed is:

1. A method of treating the human knee having a patella and musculature including vastus medialis obliquus (VMO), rectus femoris (RF), and vastus lateralis obliquus (VLO) muscles, comprising:

applying a medial force to the patella via a knee brace and permitting said medial force to track vertical and control and/or correct horizontal movements of the patella throughout the full range of knee movement, and applying a current of selected wave shape, amplitude, duration and frequency to said vastus medialis obliquus (VMO) muscle so as to stimulate and strengthen the VMO muscle and thereby correct the resulting vector force of said VMO, VLO, and RF muscles on the patella.

2. The method of treating the human knee as defined in claim 1 wherein said current is applied transcutaneously.

* * * * *